(12) United States Patent
Skogö et al.

(10) Patent No.: US 7,266,995 B2
(45) Date of Patent: Sep. 11, 2007

(54) METHOD AND INSTRUMENT FOR MEASURING SURFACE TENSION

(75) Inventors: Mårten Skogö, Stockholm (SE); John Elvesjö, Stockholm (SE)

(73) Assignee: Jenser Technology AB, Spanga (SE)

( * ) Notice: Subject to any disclaimer, the term of this patent is extended or adjusted under 35 U.S.C. 154(b) by 0 days.

(21) Appl. No.: 10/486,347

(22) PCT Filed: Aug. 9, 2002

(86) PCT No.: PCT/SE02/01446

§ 371 (c)(1),
(2), (4) Date: May 6, 2004

(87) PCT Pub. No.: WO03/014207

PCT Pub. Date: Feb. 20, 2003

(65) Prior Publication Data

US 2004/0177680 A1    Sep. 16, 2004

(30) Foreign Application Priority Data

Aug. 10, 2001  (SE) ..................... 0102701
Mar. 27, 2002  (SE) ..................... 0200954

(51) Int. Cl.
*G01N 13/00*    (2006.01)
(52) U.S. Cl. ............... 73/64.52; 73/64.48; 73/64.49; 73/64.51
(58) Field of Classification Search ............... 73/64.51, 73/64.52, 64.48, 64.49
See application file for complete search history.

(56) References Cited

U.S. PATENT DOCUMENTS 3,881,344 A * 5/1975 Jobe .......................... 73/64.51

(Continued)

FOREIGN PATENT DOCUMENTS

EP    0760472    5/1997

(Continued)

OTHER PUBLICATIONS

C. A. MacLeod and C. J. Radke, "A Growing Drop Technique for Measuring Dynamic Interfacial Tension", Academic Press. Inc. Earth Sciences Division, Lawrence Berkeley Laboratory. Jun. 8, 1993.*

(Continued)

*Primary Examiner*—Hezron Williams
*Assistant Examiner*—Samir M. Shah
(74) *Attorney, Agent, or Firm*—Nixon & Vanderhye P.C.

(57) ABSTRACT

For measuring the surface tension between a liquid and fluid such as a gas, a capillary (3, 3') is used in which the liquid slowly flows and at the end of which drops (11) are formed, falling off into a closed space (7) containing the fluid. Using a pressure sensor (5, 5') the pressure is measured which can be the absolute pressure of a fluid volume enclosed in the closed space or alternatively a differential pressure measured as the pressure difference between the liquid in the capillary and fluid contained in the closed space. The pressure is measured when one or more drops are formed and full off. The obtained pressure curves are evaluated electronically (12) and provide a value of the surface tension. The measurement can be made within a fairly short time with a high operational reliability. The temperature difference between the drop and the surrounding fluid is small resulting in a little precipitation of salts dissolved in the liquid, reducing the risk that the liquid capillary with be blocked. A pump can be connected (9) to the closed space to create a subatmospheric pressure therein and thereby assist in restarting the liquid flow through the capillary if it would be blocked. The velocity of the liquid flow to the drop can be controlled using the pump.

13 Claims, 4 Drawing Sheets

U.S. PATENT DOCUMENTS

| | | | | | |
|---|---|---|---|---|---|
| 4,196,615 | A | * | 4/1980 | Davis | 73/64.52 |
| 4,697,451 | A | * | 10/1987 | Matteson | 73/64.52 |
| 4,800,750 | A | * | 1/1989 | Enhorning | 73/64.48 |
| 4,942,760 | A | * | 7/1990 | Almeida | 73/64.48 |
| 5,479,816 | A | * | 1/1996 | Richou et al. | 73/64.48 |
| 5,503,682 | A | * | 4/1996 | Mueller-Kirschbaum et al. | 134/2 |

FOREIGN PATENT DOCUMENTS

| | | |
|---|---|---|
| EP | 1162446 | 12/2001 |
| WO | 00/00815 | 1/2000 |

OTHER PUBLICATIONS

J. Drelich, Ch. Fang and C. L. White, "Meausrement of Interfacial Tension in Fluid-Fluid Systems", Michigan Technological University, Encyclopedia of Surface and Colloid Science. 2002.*

Notification of Transmittal of International Preliminary Examination Report completed Oct. 12, 2003 and International Search Report mailed Nov. 12, 2002, In corresponding PCT Application PCT/SE2002/01446.

C. Molina, L. Victoria, and A. Arenas; "Measuring the surface tension of a liquid—gas interface by automatic stalagmometer;" In: Review of Scientific Instruments, Jun. 2000, AIP, USA, vol. 71, No. 6; pp. 2481-2486.

N. Olson, R. Synovec, W. Bond, D. Alloway, and K. Skogerboe; "Dynamic Surface Tension and Adhesion Detection for the Rapid Analysis of Surfactants in Flowing Aqueous Liquids;" Anal. Chem. 1987, vol. 69; pp. 3496-3505.

C. A. MacLeod and C. J. Radke; "A Growing Drop Technique for Measuring Dynamic Interfacial Tension;" Journal of Colloid and Interface Science, 1993; vol. 160, pp. 435-448.

K. Miller, E. Bramanti, B. Prazen, M. Prezhdo, K. Skogerboe, and R. Synovec; "Multidimensional Analysis of Poly(ethyleneglycols) by Size Exclusion Chromatography and Dynamic Surface Tension Detection;" Anal. Chem., 2000; vol. 72; pp. 4372-4380.

* cited by examiner

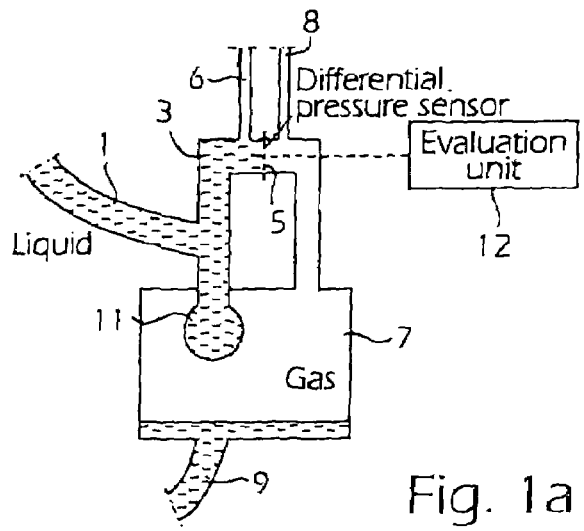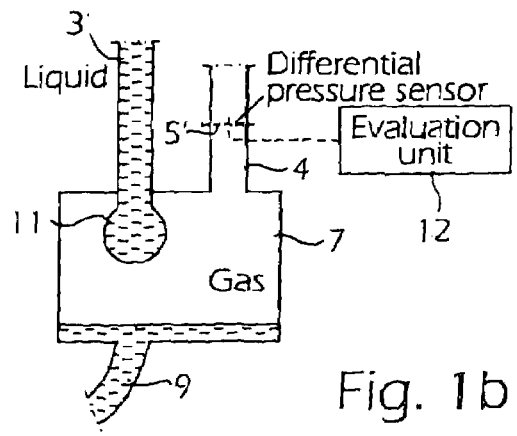
Fig. 1a  Fig. 1b
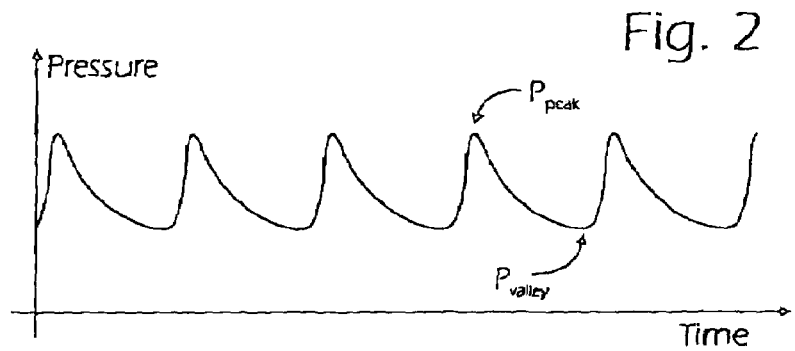
Fig. 2
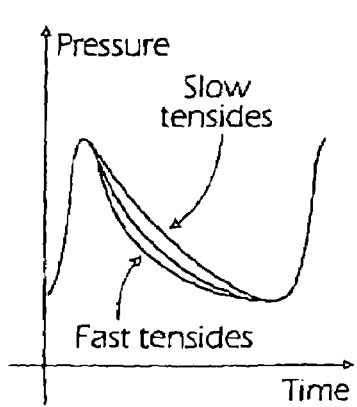
Fig. 3

METHOD AND INSTRUMENT FOR MEASURING SURFACE TENSION

This application is the US national phase of international application PCT/SE02/01446, filed in English on 09 Aug. 2002, which designated the US. PCT/SE02/01446 claims priority to SE Application No. 0102701-0 filed 10 Aug. 2001 and SE Application No. 0200954-6 filed 27 Mar. 2002. The entire contents of these applications are incorporated herein by reference.

RELATED APPLICATIONS

This application claims priority and benefit from from Swedish patent application No. 0102701-0, filed 10 Aug. 2001, and Swedish patent application No. 0200954-6, filed 27 Mar. 2002, the entire teachings of which are incorporated herein by reference.

TECHNICAL FIELD

The present invention relates to a method and an instrument for measuring surface tension by measuring pressures, for example by differential pressure measurement between a liquid and a gas.

BACKGROUND

For many different processes it is of great importance to know the magnitude of the surface tension of a liquid. The surface tension can indicate the substances present in the liquid and the concentration of known and unknown substances. By continuously measuring the surface tension, dynamically or statically, possibilities of analyzing a liquid are provided. The analysis can then for example be used to control the concentration of different substances in the liquid.

A problem existing today is that it is not possible to continuously measure surface tension in a dynamic and accurate way. The conventionally used methods of measuring surface tension are based on an external analysis of the surface tension, i.e. that a sample must be taken from the system in order that it will be possible to then make an analysis thereof. These methods result in a long time period before a response can be obtained. Of course, the drawbacks of such methods are plural, including the following ones:

Used time: Due to the fact that the measurement can not be made in the process it takes a longer time.

No possibility of immediately obtaining a response. It means that in many cases one has to wait for up to one week for a response to the question whether for example a correct tenside concentration exists in a process bath. In some cases the producing company must place the product which has already been produced in quarantine waiting for the result of the analysis. In the case of a negative response all of the already produced material must be reprocessed or in a worst case totally discarded.

Requirement of manual work. Today manual work is required when using all existing methods.

No possibility of dynamic feedback. Since it is not possible to dynamically control these processes in a feedback manner any possibility of continuously controlling the contained amounts of different substances in the process is lost.

In the article Nels A. Olson, Robert E. Synovec, William B. Bond, Dana M. Alloway, Kristen Skogeboe, "Dynamic Surface Tension and Adhesion Detection for the Rapid Analysis of Surfactants in Flowing Aqueous Liquids", Anal. Chem. 1987, Vol. 69, pp. 3496-3505 a method of measuring surface tension is described. Drops are, by a liquid flow through a capillary, formed at the end of the capillary in contact with the ambient air and the pressure the liquid is measured during the formation and the detaching of the drops from the end of the capillary. The pressure is measured by a differential pressure sensor connected both to the capillary and to the surrounding air. Disadvantages are associated with this method. For example, a temperature difference between the drops and the ambient air or gas can exist that can cause precipitation of salts which clogs the capillary.

Similar methods of measuring surface tension are described in the articles C. A. MacLeod, C. J. Radke, "A Growing Drop Technique for Measuring Dynamic Interfacial Tension", Journal of Colloid and Interface Science, 1993, Vol. 160, pp. 435-448, and Keith E. Miller, Emilia Bramanti, Bryan J. Prazen, Marina Prezhdo, Kristen J. Skogerboe, Robert E. Synovec, "Multidimensional Analysis of Poly(ethylen glycols) by Size Exclusion Chromotography and Dynamic Surface Tension Detection", Anal. Chem., 2000, Vol. 72, pp. 4372-4380.

SUMMARY OF THE INVENTION

It is an object of the invention to provide a method and a measurement instrument for measuring surface tension with a high security of operation.

It is another object of the invention to provide a method and a measurement instrument for measuring surface tension using a capillary at the end of which drops are formed.

It is another object of the invention to provide a method and a measurement instrument for measuring surface tension using measurement of pressure and by means of a capillary at the end of which drops are formed, in which measurement and instrument a reduced precipitation of salts exists and thus a smaller risk of clogging.

It is another object of the invention to provide a method and a measurement instrument for measuring surface tension based on differential measurement of pressures in a capillary.

It is another object of the invention to provide a method and a measurement instrument for measuring surface tension based on measuring pressures and by means of capillary, at the end of which drops are formed, in which method and instrument the liquid flow for forming the drops can be controlled and the flow velocity in the capillary has small fluctuations during each period when a drop is formed and falls down from the end of the capillary.

It is another object of the invention to provide a measurement instrument for measuring surface tension comprising a capillary at the end of which drops are formed and a pressure sensor in which a possible clogging of the capillary can be eliminated in a relatively simple way.

It is another object of the invention to provide a measurement instrument for measuring surface tension comprising a capillary at the end of which drops are formed and a differential pressure sensor.

In a method for detecting surface tension or interfacial tension, dynamically and statically, between a liquid and a fluid such as a gas a capillary is used in which a liquid is slowly flowing and at the end of which drops are being formed and fall down. The drops can advantageously fall off or down in a closed space containing the fluid. Using a suitable pressure sensor a measured pressure signal is generated representing the absolute pressure of a fluid or gas volume contained in the closed spaced or a differential pressure measured as the pressure difference between the liquid in the capillary and the gas or fluid contained in the closed space. The pressure signal for a time period including one or more cycles, each one of which includes that one drop is being formed and falling down from the end of the capillary is evaluated to give a value of the surface tension. In a special embodiment pressure values can be measured which then in the corresponding way can be values of the absolute pressure of a fluid or gas volume contained in the closed space or a differential pressure measured as the pressure difference between the liquid in the capillary and the gas or fluid contained in the closed space. The pressure values are then measured during a time period including one or more cycles according to the definition above and are evaluated to give a value of the surface tension.

The absolute pressure is practically measured as a pressure difference between the fluid contained in the closed space and the pressure in the surroundings of the measurement equipment, i.e. the atmospheric pressure. Generally the absolute pressure can be measured as the difference between the pressure in the closed space and some known reference pressure.

The differential pressure can generally be measured as the difference between the pressure of the fluid in the capillary and the pressure of the enclosed fluid or gas volume, i.e. on both sides of an open interfacial surface between the fluid/gas and the liquid, where the fluid/gas is enclosed in the space where the drops are formed and fall down from the end of the capillary.

Since the fluid/gas is contained in a closed space the pressure of the slowly flowing liquid, caused by a constant liquid column, will give a constant suction height or a constant feeding of the liquid, to be counteracted by the combined action of the pressure of the fluid/gas and the tension in the surface at the border between the fluid/gas and the liquid and the resistance to the flow of the liquid that is caused by the viscosity of the liquid.

By differentially measuring the pressure between the liquid in the drop and an enclosed fluid a higher security of operation is achieved than in the previously known methods and measurement instruments. The temperature difference between the drop and the surrounding fluid is smaller resulting in a smaller precipitation of salts dissolved in the liquid. The risk that a liquid capillary will be clogged is thereby reduced in the same time as condensation of the liquid inside the instrument box is avoided in which the measurement instrument otherwise would be located. These advantages are still greater in the case where a measurement is performed only of the pressure in the closed space.

A pump can be connected to the space which contains the fluid and in which the capillary ends and the drops are formed and fall down. If the capillary then contrary to what could be expected would be clogged, the pump will create a sub-atmospheric pressure in the fluid surrounding the drop, which can assist in restarting the flow of liquid through the capillary. In addition, the enclosing of the drop results in that the velocity of the liquid flow to the drop can be controlled using the pump and that the flow velocity fluctuates less during each drop formation period.

Additional objects and advantages of the invention will be set forth in the description which follows, and in part will be obvious from the description, or may be learned by practice of the invention. The objects and advantages of the invention may be realized and obtained by means of the methods, processes, instrumentalities and combinations particularly pointed out in the appended claims.

BRIEF DESCRIPTION OF THE DRAWINGS

While the novel features of the invention are set forth with particularly in the appended claims, a complete understanding of the invention, both as to organization and content, and of the above and other features thereof may be gained from and the invention will be better appreciated from a consideration of the following detailed description of non-limiting embodiments presented hereinbelow with reference to the accompanying drawings, in which:

FIGS. 1a, 1b are schematics views of the central parts of a measurement instrument for measuring surface tension by differential pressure measurement and absolute pressure measurement respectively when drops are formed, FIG. 2 is a diagram showing values of measured pressure differences as a function of time for a multitude of drops formed after each other, FIG. 3 is a diagram showing values of measured pressured differences for solutions containing various kinds of tensides.

DETAILED DESCRIPTION

Figure 4A:
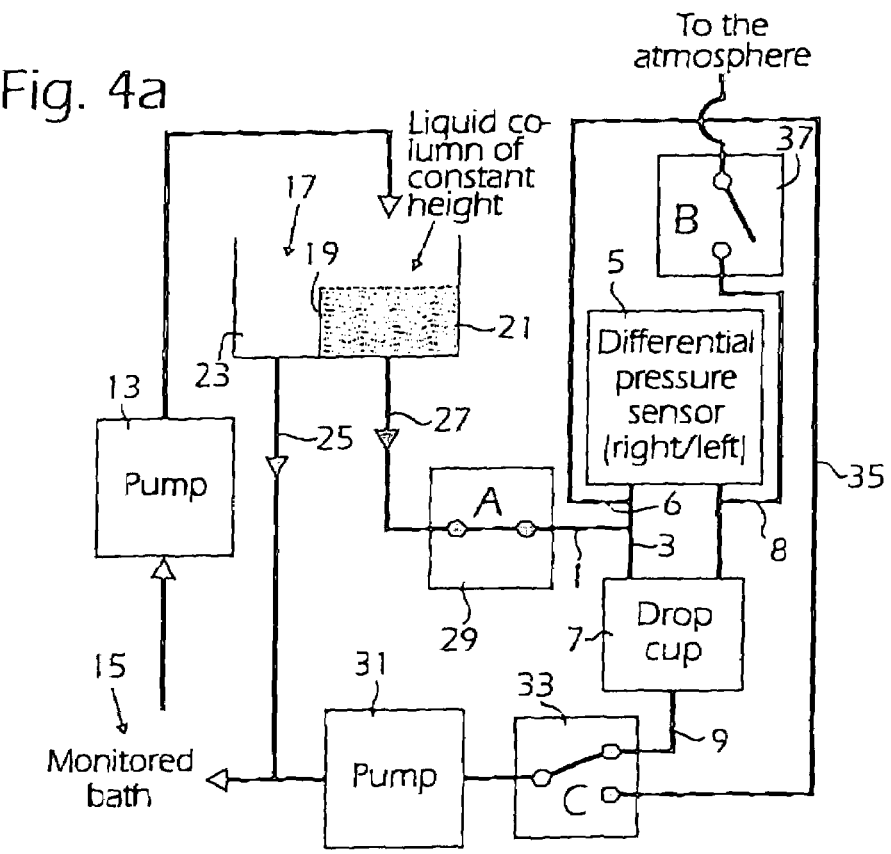
FIGS. 4a, 4b are block diagrams of measurement instruments for measuring surface tension.

In FIG. 1a the central parts of an installation for detection or measurement of surface tension, dynamically and statically, between a liquid and a gas using differential pressure measurement are shown, or generally between a first liquid having a higher, generally a significantly higher, density and a second fluid that has a lower density and can be a gas or a liquid. The liquid the surface tension of which is to be measured is fed using a substantially constant pressure from a source, not shown in this figure, through an intake pipe 1 to a side inlet in one of the for example vertically located legs of a capillary having an inverted U-shape. At the highest point of the U-shape, in its web portion, the capillary 3 is divided by a flexible diaphragm, the deflection of which can be measured using some device, not shown, coupled to the diaphragm. The measurement can be performed for example by detecting changed resistance or capacitance of suitably arranged electrically conducting parts. The diaphragm and its associated measurement circuit, not shown, form a differential pressure meter 5, see also FIGS. 4a, 5a and 6a, for measuring the pressure difference between the two ends of the capillary.

That one of the legs of the capillary 3 in which the liquid flows and to which the inlet pipe 1 is connected extends through the upper wall of a closed chamber 7 so that it has a free end portion located inside the chamber. This leg has at the free end portion an end surface at which the drops of the liquid are formed and from which they fall down. The end surface can for example advantageously be horizontal whereas the end portion can extend in a vertical direction, as has been indicated above. The other leg can end directly in the upper wall of the chamber in the bottom of which an outlet 9 is arranged. In the chamber normally some amount of the liquid stays, the surface tension of which is to be measured, and a fluid such as a gas. At the uppermost portion of the capillary on each side of the diaphragm 5, connections 6, 8 are provided for removing possibly trapped fluid or gas in the capillary 3 on the liquid side and for removing air from the closed chamber 7 through the capillary on gas side respectively.

The liquid is filled so that it fills said one leg of the capillary 3 and its web portion up to the diaphragm 5 without trapping any amount of gas or some other substance at the diaphragm. The liquid slowly flows down by its own weight or possibly assisted by a pump, not shown in this figure, through the leg and forms drops 11 at the mouth of the leg, which one after the other falls down towards the bottom of the chamber 7. Then, the differential pressure that is recorded by the diaphragm 5 varies periodically, see the discussion below. The differential pressure curve or signal is taken for one or advantageously a plurality of periods, i.e. for a plurality of fallen drops, and is evaluated in an evaluation device 12, suitably a computer or microprocessor. From the curve or signal, among other things the surface tension can be derived, see the discussion below. Generally, the pressure measured using the differential pressure measurement is a function of primarily the surface tension of the drop at its interfacial surface to the fluid enclosed in the chamber, the size of the drop, the viscosity and the flow velocity of the liquid and the size of the portion of the capillary located between the drop 11 and the diaphragm in the pressure sensor or the liquid inlet to the capillary 3.

In order to try to explain the most basic theory of the pressure measurement the liquid drop can be thought of as resembling a balloon. The pressure in a balloon depends on the tension in its surface and on the size of the balloon. It is always most difficult to blow in the first amount of air when one is inflating a balloon. This depends on the fact that the surface of a small balloon is made to expand very much for each amount of air that enters the balloon. The area of a large balloon does not expand as much.

The size of the balloon thus determines the amount of new interfacial area that is created when a certain amount of air is blown into the balloon, whereas the tension in the surface of the balloon is the factor that determines the amount of energy that is required to create this new interfacial area.

In the same way the pressure inside a liquid drop is a function of the size of the drop and its surface tension. This relation can in the case where the drop is supposed to be a perfect sphere or semisphere be written:

$$P_\gamma = \gamma \cdot dA/dV = \gamma \cdot 2/r$$

where $P_\gamma$ is the pressure in the drop 9 resulting from the surface tension, $\gamma$ is the surface tension in the interfacial surface of the drop, A, V, and r denote the interfacial area of the drop to the gas in the chamber 7, the volume of the drop and its radius respectively.

The pressure measured at the sensor diaphragm 5 is also affected by the viscosity of the liquid that is investigated. The pressure drop in the capillary caused by the viscosity is given by:

$$P_\eta = 8\eta LF/(R^4\pi)$$

where $P_\eta$ is the pressure resulting from the viscosity $\eta$ of the liquid, L is the length of the portion of the capillary 3 that is located between the mouth of the inlet pipe 1 in the capillary and the lowermost point of the drop from which the liquid flows. F is the volume flow velocity of the liquid and R is the internal radius of the capillary.

The pressure measured using the differential pressure measurement in the installation according to FIG. 1a is a function of primarily the surface tension of the drop, its size, the viscosity and the flow velocity of the liquid and the size of the capillary between the drop and the pressure sensor. This pressure is thus given by:

$$P = k_1 \cdot \gamma/r + k_2 \cdot \eta \cdot F + k_3$$

where $k_1$, $k_2$ and $k_3$ are constants. The constant $k_3$ results from the fact that the sides of the diaphragm included in the pressure sensor 5 are affected in different amounts by the pressure from for example a standing liquid column and by the fact that the zero level of the detector, such as is conventional, is set not considering this fact.

Using a continuous differential pressure measurement repeated pressure profiles of the growth of drops are obtained, see the diagram of FIG. 2. From these drop profiles information on the surface tension and viscosity of the liquid can be obtained. In the case where tensides are present, information can also be derived on the velocity, with which they move from the bulk of the liquid to the interfacial surface of the liquid, from the measured pressure profiles, see FIG. 3.

In the case where the liquid flow is supposed to be constant, the influence of the viscosity on the measured pressure is constant, so called static surface tension. For sufficiently small flow velocities also the surface tension in the drop can be supposed to be constant. Thus, in this special case the drop size is supposed to be the only quantity that varies in time.

The pressure difference between a peak and a valley is then given by:

$$\Delta P = P_{peak} - P_{valley} = \gamma \cdot 2(1/r_{min} - 1/r_{max})$$

where $P_{peak}$ and $P_{valley}$ are the highest and the lowest measured pressure respectively during one drop profile, and $r_{min}$ and $r_{max}$ are the drop radii at the corresponding occasions. According to the discussion above the pressure in the drop has its largest value when the drop is smallest, i.e. when the radius of curvature of the drop is smallest. This happens when the drop only is a semisphere that is suspended at the end of the capillary. The highest pressure measured is thus for the same drop size, $r_{min}$, always independent of surface tension and thus a function only of the surface tension.

In the case where $r_{min} \ll r_{max}$ it is thus true that:

$$\Delta P \approx \gamma \cdot 2/r_{min} = k_4 \cdot \gamma$$

where $k_4$ is a constant.

Furthermore, for these assumptions the following is true:

$$P_{valley} \approx k_5 \cdot \eta + k_3$$

for a suitably selected constant $k_5$, since the pressure contribution from the surface tension can be assumed to be zero when the drop is detached from the capillary.

For these simplified assumptions thus the values of the constants $k_3$, $k_4$ and $k_5$ can be determined by making a calibration using two liquids having known surface tensions and viscosities. Thereupon, the surface tension and the viscosity of an arbitrary liquid can be determined from the information of the amplitudes of the peaks and valleys in a given pressure profiles for the drops in an apparatus according to FIG. 1a.

The measurement instrument shown in FIG. 1a can be somewhat simplified by instead of performing a measurement of the difference between the pressure of the lighter fluid contained in the chamber 7 and the pressure in the capillary at the inlet side, i.e. measurement of a genuine differential pressure, only measuring the pressure in the chamber. The pressure in the chamber can in the simplest manner be measured as a pressure difference between the chamber pressure and the pressure in some reference volume, where the latter pressure in this case can be taken as the atmospheric pressure. Such a measurement instrument is schematically shown in FIG. 1b. The capillary 3' can here be made as a straight piece of piping which at its inlet end is connected to the liquid inlet 1 and at its outlet end in the same way as above ends inside the chamber 7. The portion of the capillary at its end inside the chamber can advantageously be substantially vertical and pass through the upper wall of the chamber so that the end of the capillary is located freely in the upper portion of the chamber, at a distance of possible liquid contained in the chamber. To the chamber, for example also through the upper surface or wall thereof, also an end of a line 4 is connected, the other end of which is open to the ambient air or atmosphere and in which the differential pressure sensor 5' is placed. Any evacuation of the capillary 3' and in particular its region between the inlet for liquid from the line 1 and the diaphragm in the differential pressure measurement sensor is not needed here.

Using the measurement instrument according to FIG. 1d measured pressure curves are obtained similar to those shown in FIG. 2. From them the surface tension can be determined in the same way as has been described above by making a calibration using liquids having known data. The obtained measured value of the surface tension can have a somewhat lower accuracy in this case.

A measurement instrument or measurement installation based on the method described above with reference to FIG. 1a can for example be constructed as is illustrated by the block diagram of FIG. 4a. A pump 13 pumps liquid for which a measurement is to be made from a monitored bath 15 containing liquid to a container 17 placed on a horizontal level above the level of the chamber 7. In the container 17 the upper level of the liquid has always a constant height, this being provided using some overflow device such a spillway. The overflow device comprises a partition wall 19 in the container 17 dividing it in a first chamber 21 that is filled with liquid up to the upper edge of the partition wall and a second chamber 23. The second chamber has a bottom outlet that by a line 25 returns liquid that has flown over to the bath 15. The first chamber 21 has also a bottom outlet that through a line 27 including a first valve 29 of the on-off type connected therein is coupled to the inlet line 1 for liquid to the capillary 3. The constant level in the first chamber 21 in the container 17 provides a constant pressure of the flow of liquid fed into the capillary 3. This means that the inflow of liquid forming drops, due to the influence of the surface tension, is not totally constant but, however, in a good approximation.

Furthermore, a second pump 31 is provided that is connected to a second valve 13 of the switching type to pump in the direction from this valve towards the bath 15. One of the inlets of the valve 13 is connected to the outlet 9 of the drop chamber 7 and the other inlet is connected to a line 35 extending from the bleeding connection 6 of the capillary 3 on the liquid side. The ventilation connection 27 on the gas side is connected to a first end of a third valve 37 of the on-off type, the other end of which is connected to the ambient air.

When using the installation according to FIG. 4a for measurement of surface tension or for recording the pressure profile the valves have the illustrated positions. The first valve 29 is then in such a position that liquid is directed to the inlet 1 of the drop chamber. The second valve is set so that it connects the second pump 31 to pump liquid out of the bottom of the drop chamber 7. The third valve 37 is set so that the drop chamber 7 is completely separated from the ambient air. Where starting the installation, the first valve 29 is set to shut off the feeding of liquid to the capillary 3, the second valve 33 is set to a position for connecting the drop cup 7 to the second pump 31 and the third valve 37 is opened to connect the drop chamber to the ambient air. The pump 31 in that way cleans the gas side in the pressure sensor 5 at the same time as its empties the drop cup 7 from possible liquid remaining from the previous measurement. Thereupon, all the three valves 29, 33, 37 are reset to their opposite positions. In thus position the pump 31 fills the liquid side of the differential pressure sensor 5 by sucking liquid from the container 17 through the line 27 and further through the capillary 3 to the connector 6. Thereupon the valve 33 is again set to be in direct contact with the drop cup 7 after which the instrument is ready to provide measured data.

Blocking of the capillary 3 is avoided by the weak subatmospheric pressure in the drop chamber 7 created by the pump 31. The pumping speed of this pump can be set so that a substantially constant liquid flow to the drop chamber is obtained and hence a constant volume of the gas enclosed in the drop chamber.

Figure 4B:
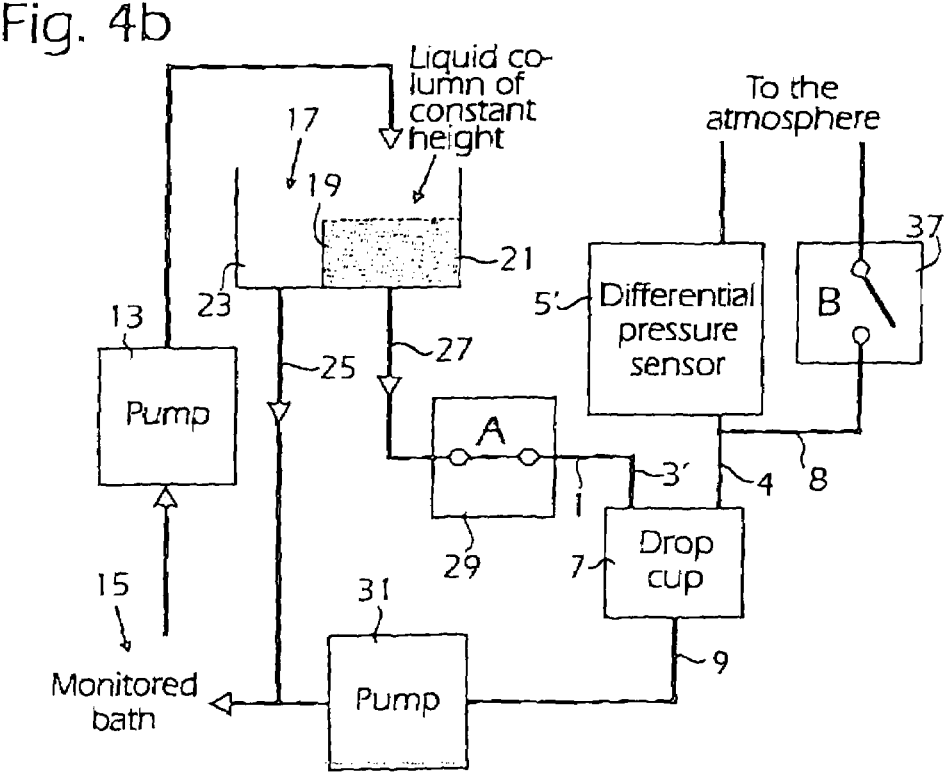

An installation that instead uses measurement of the pressure in the chamber 7 in relation to the ambient pressure is shown by the block diagram of FIG. 4b. It agrees with the block diagram of FIG. 4a except the connection terminal 6, the line 35 and the valve 33 being excluded and the coupling of the capillary 3' to the pressure sensor 5' being interrupted.

Figure 5A:
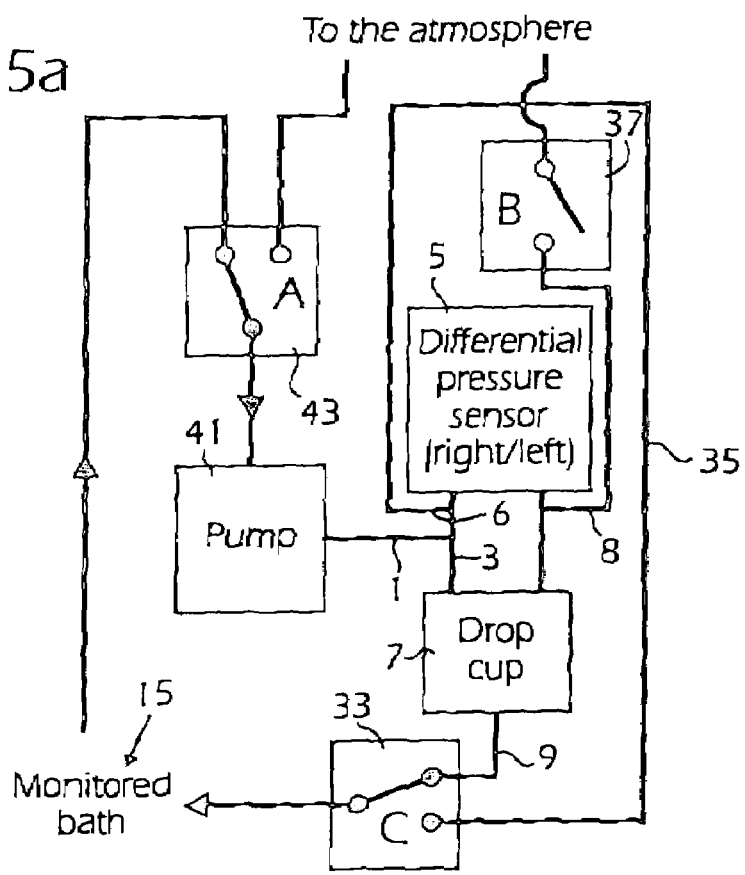
FIGS. 5a, 5b are block diagrams of alternative embodiments of measurement instruments for measuring surface tension.

In the installation according to FIG. 5a that is arranged for measuring differential pressures according to FIG. 1a only a single pump 41 is used. It is through a valve 43 of switching type connected to the bath 15. The valve 43 can also be set so that one of its inlets which is connected to the ambient air becomes connected to the outlet of the valve and hence the pump 41. The pressure side of the pump 41 is connected to the inlet pipe 1. In other details the installation agrees with that shown in FIG. 4a except the pump 31 being excluded. In the shown positions of the valves the installation is operative for measuring the pressure profiles during the drop formation. The pump 41 feeds liquid to the capillary 3 and therefrom further on to the drop chamber in which the drops are formed. The valve 33 is normally in such a position that the outlet of the chamber 7 is through the valve connected to the bath 15.

When starting the installation first the valve 33 is reset. The pump 41 then sucks air through this valve and presses the air through the capillary 3 into the drop chamber 7 and pumps away all liquid therefrom to the bath 15. The valve 43 is then reset so that liquid from the bath is pumped into the capillary 3 and the drop chamber 7. The valve 33, connected to the outlet line of the chamber 7, is set, so that one of its inlets, that is now is connected to its outlet, is connected to the line 35 coupled to the bleeding nipple on the liquid side of the pressure sensor 5. The pump 41 presses liquid into the capillary 3, and this liquid in turn presses air away from the liquid side in the pressure sensor 5 to the line 35 and hence to the bath 15 through the valve 33. Thereupon, the valve 43 is reset to its operative position as is shown in the figure.

Figure 5B:
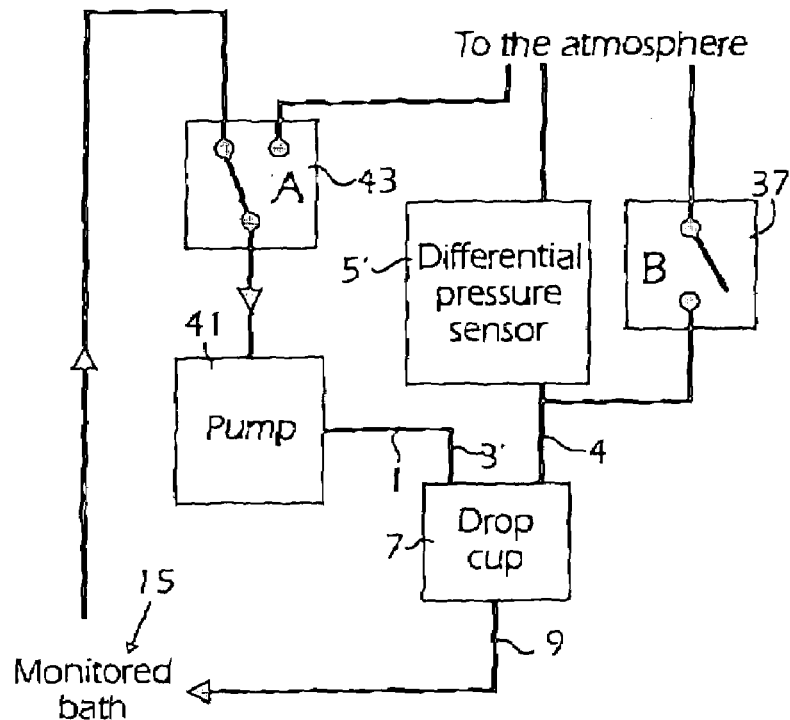

The installation including only one pump can also in a simple way be changed from measuring the pressure difference between the chamber 7 and the atmosphere as is shown by the block diagram of FIG. 5b. The block diagram in FIG.

5b agrees with the block diagram of FIG. 5a except the connection terminal 6, the line 35 and the valve 33 being excluded and the capillary 3' not being connected to the pressure sensor 5'.

The embodiments according to FIGS. 5a, 5b have some drawbacks due to the fact that the feeding of the capillary 3, 3' is achieved using a pump 41 what can cause interfering pressure variations in the capillary and in the gas ill the drop chamber 7. Also, a constant liquid level in the drop chamber cannot be maintained in a simple way. However, these simpler embodiments can be used in those cases where a high measurement accuracy is not required.

Figure 6A:
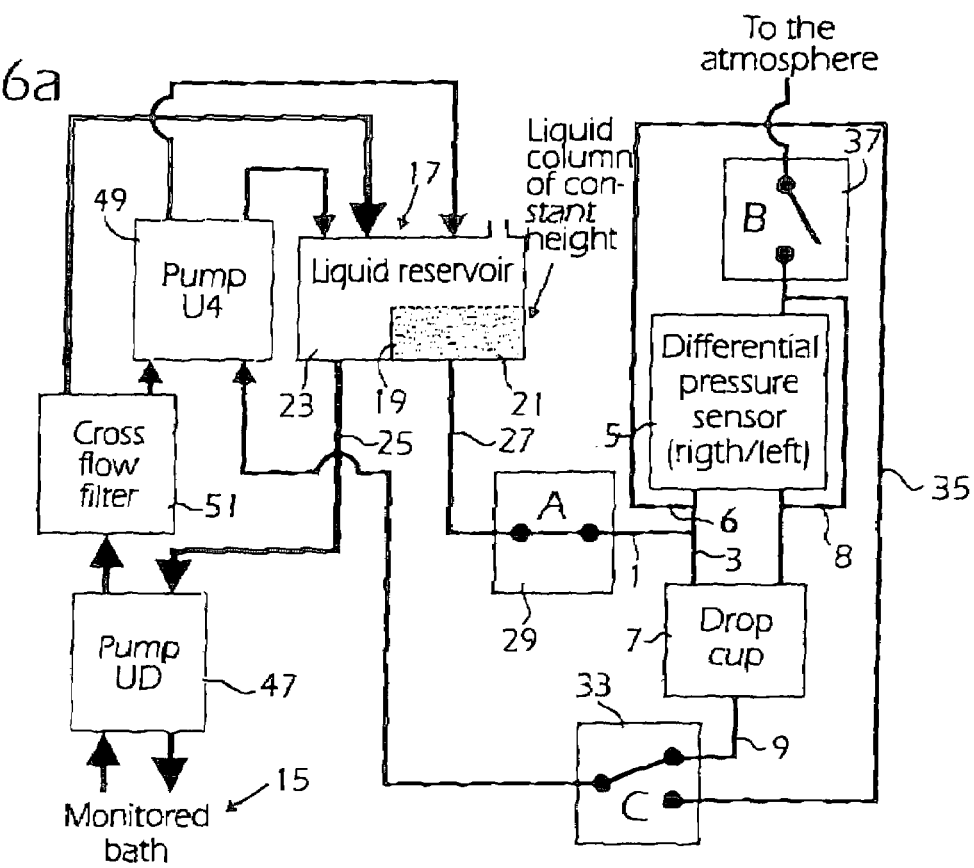
FIGS. 6a, 6b are block diagrams of still other alternative embodiments of measurement instruments for measuring surface tension.

Another embodiment of an installation for measuring the measure profiles in drop formation for the case of measuring the difference between the pressures in the capillary 3 and in the chamber 7 is shown by the block diagram of FIG. 6a. Here, two double hose pumps 47, 49 are used. The first hose pump 47 pumps on its first side liquid from the bath 15 to a filter 51 of crossflow type in which possible particles in the liquid are removed. From the filter 51 the major, non-filtered portion of liquid is provided to the outflow chamber, the second chamber 23 in the container 17. The container 17 is made including an spillway 19 as in the embodiment according to FIG. 4a which delimits the first chamber 21 from the second chamber 23. From the latter chamber, i.e. the outflow chamber, the liquid is pumped back to the bath 15 by the second side of the first pump 47. The filtered portion of the liquid from the filter 51 is conducted to the first side of the second hose pump 49 and is hence pumped to the first chamber 2l in the container 17, in which thereby and due to the overflow device 19 a constant liquid level is maintained. The second side of the second pump 49 is connected to the outlet side of the second valve 33 to slowly pump, in the measuring state of the installation, liquid from the drop chamber 7 to the outlet chamber 23 in the container 17. If the second valve 33 is reset, instead liquid is pumped from the highest point of the capillary 3 on the liquid side of the pressure sensor 5, i.e. from the connection terminal 6, to evacuate gas from the liquid side of the pressure sensor. Other parts of the installation are made as the corresponding parts of the installation according to FIG. 4a and works in the same way as them.

In a practical embodiment according to FIG. 6a the differential pressure sensor 5 was of the type LPM 8381 from the company Druck. This sensor has a measuring range of 0-10 mbar. It is supplied with a voltage of 24 V DC and gives a signal of 0-10 V. Through the thin capillary the pressure detector 5 was connected to the drop cup 7 that had an interior volume of 16.5 ml. The signal from the sensor 5 was provided to electronic circuits, not shown, comprising a 12-bit A/D converter, of the type ADS7816 from the company Burr-Brown, controlled by a microprocessor of the type Atmega103 from the company Atmel having a clock frequency of 3.6864 MHz. In the installation, two hose pumps 47, 49 were included each having two channels and manufactured by the company Watson Marlow Alitea and specially made to fulfill the demands of the measuring installation. The channel or side of the second hose pump 49 that pumped liquid from the drop cup 7 gave a flow of approximately 1 ml liquid per minute through the drop cup.

Figure 6B:
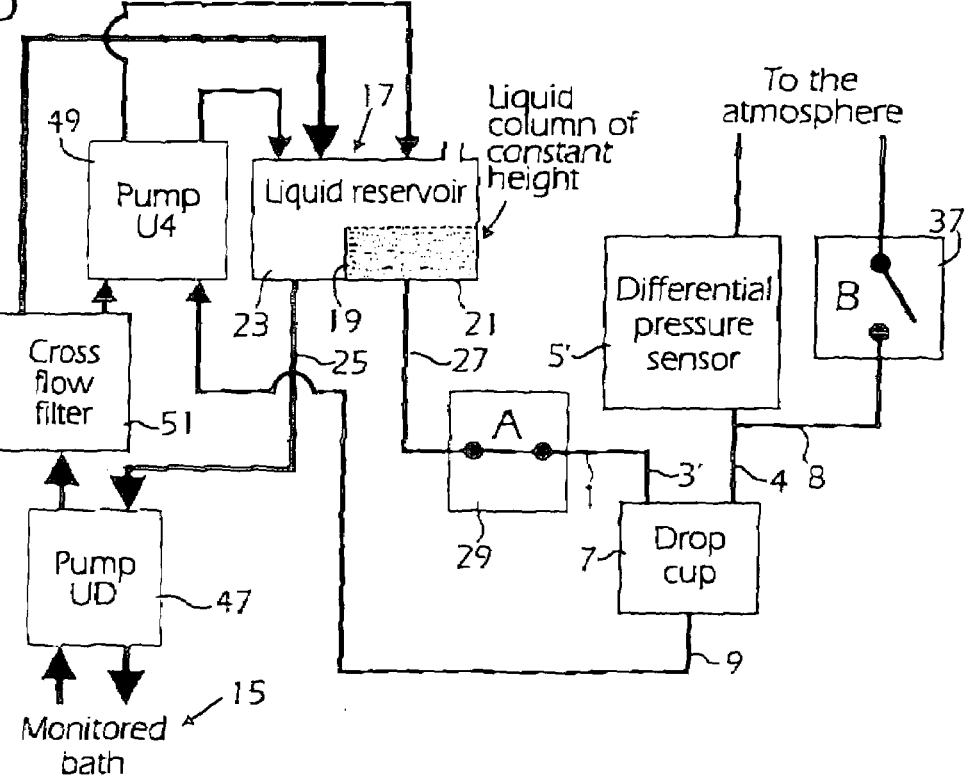

The installation according to FIG. 6a can in the same way as above be modified for measuring the difference between the pressure in the chamber 7 and the atmospheric pressure, as is shown by the block diagram of FIG. 6b. The block diagram of FIG. 6b agrees with the block diagram of FIG. 6a except the connection terminal 6, the line 35 and the valve 33 being excluded since they are not needed and further the connection of the capillary 3' to the pressure sensor 5' being excluded.

While specific embodiments of the invention have been illustrated and described herein, it is realized that numerous additional advantages, modifications and changes will readily occur to those skilled in the art. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention.

The invention claimed is:

1. A method of measuring surface tension at the interfacial surface between a liquid and a fluid, the liquid having a larger density than the fluid and being substantially non-miscible therewith, the method including:
   having the liquid flow in one direction through a capillary for forming successive liquid drops that are denser than the fluid at an end of the capillary positioned in a closed space in a vessel containing the fluid, wherein the formed successive drops fall from the end of the capillary and are received in the closed space,
   measuring a pressure of the fluid in the closed space with the closed space disconnected from the atmosphere so that the pressure measured in the closed space is independent of the atmospheric pressure to provide a pressure measurement signal while the liquid is flowing through the capillary and is forming drops, and
   evaluating the pressure measurement signal to provide a value of the static surface tension between the liquid and the fluid in the closed space.

2. The method of claim 1, wherein, in measuring the pressure of the fluid in the closed space, the pressure of the fluid in the closed space is measured as a relative pressure being the difference between the absolute pressure of the fluid in the closed space and the pressure in the liquid in the capillary.

3. The method of claim 1, wherein, in measuring the pressure of the fluid in the closed space, the measurement is performed by measuring the absolute pressure of the fluid in the closed space.

4. The method of claim 1, wherein, in having the liquid flow through the capillary, liquid is continuously pumped away from the closed space to allow that new drops are formed.

5. The method of claim 4, wherein the liquid is continuously pumped away from the closed space with such a velocity that substantially a constant flow velocity in the capillary is obtained.

6. The method of claim 1, wherein, in having the liquid flow through the capillary, the liquid is provided in a free flow from a liquid container having an upper liquid surface located at a constant horizontal level above the level of an inlet of the capillary.

7. The method of claim 1, wherein, in having the liquid flow through the capillary, the liquid is pumped from a liquid container into the capillary.

8. An instrument for measuring the surface tension at the interfacial surface between a liquid and a fluid, the liquid having a greater density than the fluid and being substantially non-miscible therewith, the instrument comprising:
   a vessel having a closed space containing the fluid, a device for feeding the liquid, a capillary connected to the feeding device and having a first end located in the closed space, wherein the device and the capillary are arranged so that the liquid flows through the capillary and forms successive drops at the first end that fall off from the first end of the capillary and are received in the closed space, a pressure sensor connected to the closed space for measuring the pressure of the fluid in the closed space with the closed space disconnected from the atmosphere so that the pressure measured in the closed space is independent of the atmospheric pressure when the drops are being formed and fall off to produce a pressure measurement signal, and an evaluation device for receiving and evaluating the pressure measurement signal to provide a value of the static surface tension between the liquid and the fluid in the closed space.

9. The instrument of claim 8, wherein the pressure sensor is of a differential type and at a first side is connected to the closed space and at a second side is connected to the capillary to measure the pressure of the fluid in the closed space as a relative pressure between an absolute pressure of the fluid in the closed space and the absolute pressure of the liquid in the capillary.

10. The instrument of claim 8, further comprising a pump connected to an outlet of the closed space for pumping the liquid away from the closed space.

11. The instrument of claim 10, wherein the pump is arranged to pump liquid away from the closed space with a constant velocity so that a substantially constant flow through the capillary is maintained.

12. The instrument of claim 8, wherein the feeding device includes a liquid container connected through a line to the capillary and having an upper liquid surface located at a constant horizontal level above a level of an inlet of the capillary.

13. The instrument of claim 8, wherein the feeding device comprises a liquid container and a pump for pumping liquid from the liquid container to the capillary.

* * * * *